United States Patent [19]
Dilk et al.

[11] Patent Number: 6,037,473
[45] Date of Patent: Mar. 14, 2000

[54] USE OF SUBSTITUTED BENZAZOLES AS UV ABSORBERS, NEW BENZAZOLES AND PROCESSES FOR THEIR PREPARATION

[75] Inventors: Erich Dilk, Holzminden; Roland Langner, Bevern; William Johncock, Heinsen, all of Germany

[73] Assignee: Haarmann & Reimer GmbH, Holzminden, Germany

[21] Appl. No.: 09/298,317

[22] Filed: Apr. 23, 1999

Related U.S. Application Data

[62] Division of application No. 08/969,331, Nov. 13, 1997.
[51] Int. Cl.[7] ............ C07D 417/04; C07D 413/04; C07D 403/04
[52] U.S. Cl. ............ 548/159; 548/217; 548/305.4
[58] Field of Search ............ 548/159, 217, 548/305.4

[56] References Cited

U.S. PATENT DOCUMENTS

| | | |
|---|---|---|
| 3,751,563 | 8/1973 | Richardson . |
| 4,387,089 | 6/1983 | De Polo . |
| 4,429,133 | 1/1984 | Littlewood . |
| 5,585,091 | 12/1996 | Pelzer et al. . |

FOREIGN PATENT DOCUMENTS 0 669 323 A1   8/1995   European Pat. Off. .

OTHER PUBLICATIONS

Comprehensive Heterocycle Chemistry, vol. 5., p. 387.

Acta Pharamceutica Turcica vol. XXXIII (1991) pp. 35–39.

J. Chem. Soc. (C) (1967) pp. 33–39.

J. Chem Soc. (1928) pp. 2393–2399.

Chemical Reviews, vol. 74, No. 3, (Jun. 1973) pp. 279–314.

*Primary Examiner*—Robert Gerstl
*Attorney, Agent, or Firm*—Joseph C. Gil; Noland J. Cheung

[57] ABSTRACT

The invention relates to N-substituted benzazoles, processes for their preparation and their use as UV absorbers.

1 Claim, No Drawings

USE OF SUBSTITUTED BENZAZOLES AS UV ABSORBERS, NEW BENZAZOLES AND PROCESSES FOR THEIR PREPARATION

This is a divisional application of Ser. No. 08/969,331, filed Nov. 13, 1997.

The invention relates to the use of N-substituted benzazoles as UV absorbers, to new N-substituted benzazoles and to processes for their preparation.

UV absorbers are compounds having a pronounced absorbancy for ultraviolet radiation. They are used in particular as sunscreens in cosmetic and pharmaceutical preparations, but also for enhancing the photostability of industrial products such as paints, varnishes, plastics, textiles, packaging materials and rubbers.

UV rays are classified according to wavelength into UV-A rays (320–400 nm, UV-A-I: 340–400 nm, UV-A-II: 320–340 nm) or UV-B rays (280–320 nm). In very general terms the following is true: The damaging effect of the UV rays on human skin rises with decreasing wavelength and increasing duration of exposure.

UV rays can cause acute and chronic skin damage, the nature of the damage depending on the wavelength of the radiation. For instance, UV-B radiation can cause damage ranging from sunburn (erythema) up to very severe skin burns. Reductions in enzyme activities, disruptions to the DNA structure and alterations of the cell membrane are other known damaging effects of UV-B rays. The UV-A rays penetrate into relatively deep skin layers, where they can accelerate the ageing process of the skin. The shorter-wave UV-A-II radiation additionally intensifies the development of sunburn. Furthermore, the UV-A radiation may elicit phototoxic or photoallergic skin reactions.

Very frequent and unprotected irradiation of the skin with sunlight leads to a loss in skin elasticity and to increased formation of wrinkles. In extreme cases, pathological skin changes are observed, up to and including skin cancer.

In accordance with the position of their absorption maxima UV absorbers are sub-divided into UV-A and UV-B absorbers, if a UV absorber absorbs both UV-A and UV-B, it is referred to as a UV-A/B broadband absorber.

There is a range of effective UV-B absorbers, examples being 2-ethylhexyl p-methoxycinnamate, isoamyl p-methoxycinnamate, phenylbenzimidazole sulfonic acid (and its salts) and 3-(4'-methyl-benzylidene)camphor.

The number of suitable UV-A absorbers is much smaller, and they have considerable deficiencies:

For instance, 4-tert-butyl-methoxy-dibenzoylmethane and 4-isopropyl-dibenzoylmethane (DE-A 2 945 925) are not very photostable. In addition, they are of only limited solubility in cosmetic oils, which may lead to problems in the formulation of cosmetic preparations. Sun protection products containing dibenzoylmethane derivatives, moreover, may on textiles leave marks which are extremely difficult to wash out.

The benzophenones used as UV-A/B broadband absorbers do not have the desired broad UV-A and UV-B absorption or possess only slight absorption within this region. For example, 2-hydroxy-4-methoxybenzophenone (U.S. Pat. No. 3,751,563) exhibits only a relatively low absorption in the short wave UV-A-II region. In addition, the solubility of the benzophenones in cosmetic oils is limited.

In order to obtain an effective protective effect over the entire ultraviolet range, therefore, it is common to combine different UV filter substances which supplement each other in their absorbency.

Photostable UV-absorbers are sought which have a broad absorption range and which, owing to strong absorption, provide effective protection against the damage due to UV-A and UV-B rays. For use in cosmetic sunscreen compositions, moreover, these UV absorbers should meet the following criteria:

in the case of crystalline UV absorbers, good solubility in cosmetic solvents and liquid, oil-soluble UV absorbers for example ethyl, isoamyl and isooctyl p-methoxycinnamate, ethylhexyl salicylate, homomenthyl salicylate, menthyl anthranilate, ethylhexyl p-aminobenzoate, ethyl and ethylhexyl 3,3-diphenyl-2-cyanoacrylate;

liquid, oil-soluble UV absorbers should be readily miscible with other UV absorbers and cosmetic oil components;

water-resistant UV protection;

trouble-free processability in cosmetic formulations and stability under conditions of use;

compatibility with cosmetic base materials;

pH stability;

thermal stability;

no staining of textiles, or none that cannot be washed out without problems;

colorlessness and odor neutrality.

The invention relates to the use of compounds of the formula

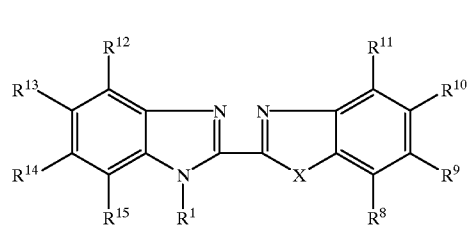

(I)

in which

X is S, NH, $NR^1$ or O, $R^1$ is $C_1$–$C_{20}$-alkyl, $C_2$–$C_{20}$-alkenyl, $C_3$–$C_{15}$-cycloalkyl, $C_6$–$C_{12}$-aryl, $C_6$–$C_{12}$-ar-$C_1$–$C_6$-alkyl, $C_1$–$C_{20}$-alkoxycarbonyl or $C_5$–$C_{12}$-hetaryl, it being possible for these substituents to be substituted by $C_1$–$C_6$-alkyl, $C_1$–$C_{16}$-alkoxy, $C_6$–$C_{12}$-aryloxy, amino, hydroxyl, $CONR^2R^3$, $COOR^4$ or $Si(OR^7)_3$ or to be interrupted by ether oxygen, $R^2$ and $R^3$ independently of one another are H or $C_1$–$C_{16}$-alkyl, $R^4$ is H, $C_1$–$C_{16}$-alkyl, $C_6$–$C_{12}$-aryl or $R^5$—O—($CH_2$—$CH(R^6)$—O—)$_n$—$CH_2$—$CH(R^6)$—, $R^5$ is $C_1$–$C_4$-alkyl, $R^6$ is H or methyl, n is zero or an integer from 1 to 4, $R^7$ is $C_1$–$C_4$-alkyl and $R^8$ to $R^{15}$ independently of one another are hydrogen, amino or nitro or possess the meaning given under $R^1$ as UV absorbers.

A further subject of the invention is compounds I in which $R^1$ is $C_5$–$C_{20}$-alkyl, preferably $C_5$–$C_{12}$-alkyl, especially 2-ethylhexyl.

Preferred compounds I are those in which $R^1$ is optionally substituted alkyl, particular preference being given to branched alkyl substituents.

Particularly preferred compounds I are those in which $R^1$ is $C_4$–$C_{12}$-alkyl, cyclohexyl-$C_1$–$C_6$-alkyl, benzyl or $C_1$–$C_{12}$-alkoxycarbonyl-$C_1$–$C_3$-alkyl.

Other particularly preferred compounds I are those in which X is O, S or $NR^1$ and $R^1$ is $C_4$–$C_{12}$-alkyl, cyclohexyl-$C_1$–$C_6$-alkyl, benzyl, $C_1$–$C_4$-alkoxycarbonyl-$C_1$–$C_3$-alkyl or $C_6$–$C_{12}$-aryl.

The compounds of the formula I can be prepared by analogy with known processes; in this regard compare, for example, Comprehensive Heterocyclic Chemistry (Editor K. T. Potts, Pergamon Press, 1984), Vol. 5, 387f; Preston, P. N., Chem. Rev. 74, 279 (1974); Demirayak, S., Acta Pharm. Turc. 1991, 33(2), 35; Ennis, B. C., Holan, G. and L., J. Chem. Soc., C. 1967(1), 33. By way of example, three possible preparation processes are indicated below:

Route A:

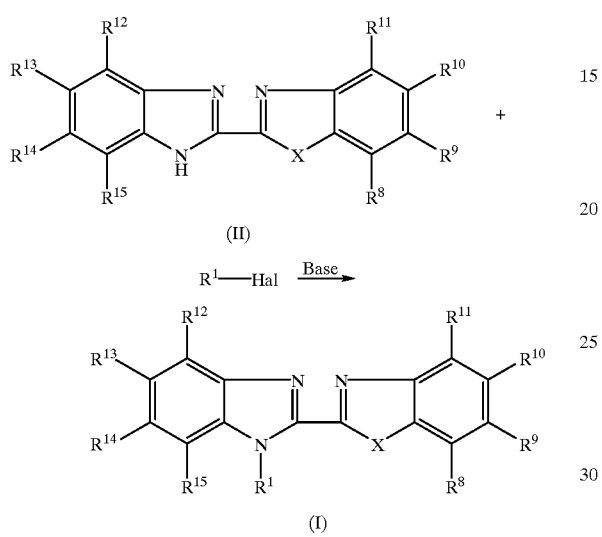

(II)

$R^1$—Hal $\xrightarrow{\text{Base}}$ (I)

Compounds of the formula I can be obtained by alkylating nitrogen-unsubstituted benzimidazolebenzazoles with organyl halides.

The N-unsubstituted benzimidazolebenzazoles used as precursors are obtainable, for example, by reacting 2-trichloromethylbenzimidazole with o-phenylenediamine, o-aminophenol or o-aminothiophenol. Bisbenzimidazoles can also be prepared advantageously by heating o-phenylenediamine with trichloroacetic acid in dilute hydrochloric acid.

The organylation is conducted under alkaline conditions, where alkali metal and alkaline earth metal hydrides, alcoholates, hydroxides or carbonates can be used as bases, and with preferably from 1.0 to 3.0 mol, in particular from 1.0 to 1.5 mol, of base being used per mole of II. In general from 1.0 to 4.0 mol, preferably from 1.0 to 2.0 mol, of the organyl halide are employed.

The organylation is preferably conducted in organic aprotic solvents, for example dimethylformamide or dimethyl sulfoxide, but can also be performed in alcohols, ethers such as dioxane, ketones such as acetone, aromatic hydrocarbons such as toluene, or liquid ammonia.

The reaction temperature can be in the range between 20 and 200° C., in particular between 60 and 140° C.

After the end of the reaction the product can be precipitated by addition of water and can be purified by recrystallization and/or column chromatography.

Route B:

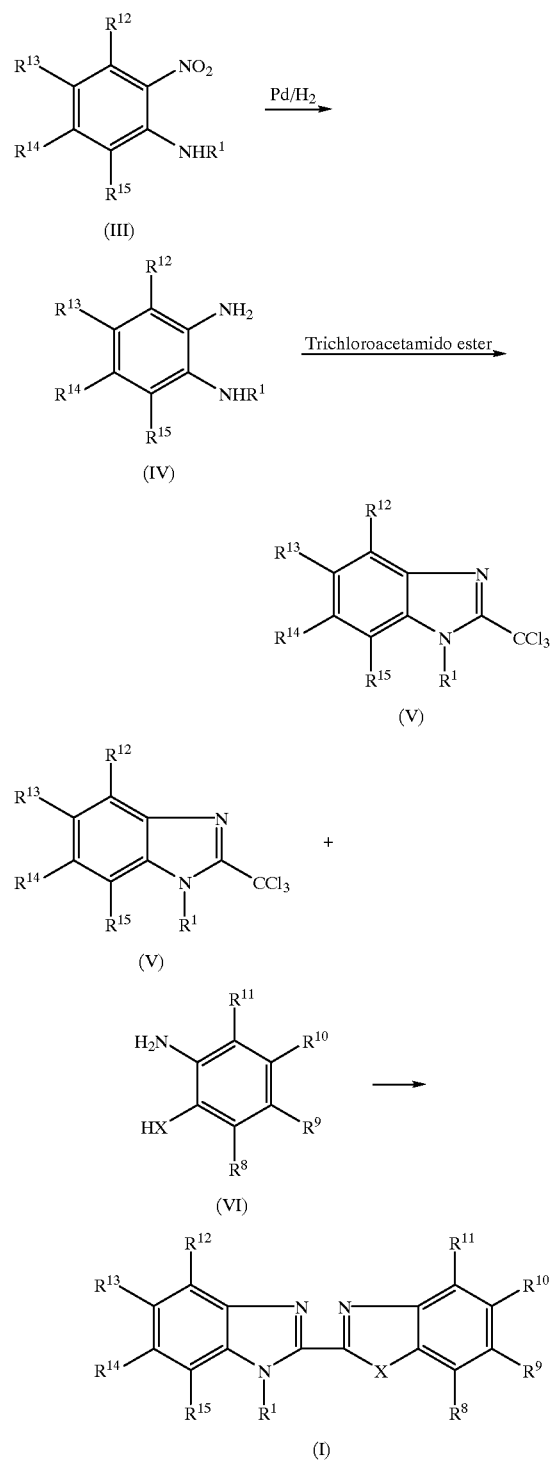

From the respective nitro compounds III, N-substituted o-phenylenediamines IV are obtainable by hydrogenation by means of Pd/C. These diamines IV can be converted with an equimolar amount of trichloroacetimido ester in acetic acid into the corresponding 2-trichloromethylbenzimidazoles V. The reaction takes place at room temperature in from 5 to 20 hours. The products can be precipitated by addition of water.

By reacting 1 mol of 2-trichloromethylbenzimidazole V with from 1.0 to 1.5 mol of o-phenylenediamine, o-aminophenol or o-aminothiophenol VI, compounds of the formula I are obtained. The reaction can be performed at temperatures between 5 and 120° C., preferably from 20 to 80° C., in alcohols as solvents; the reaction time can be from 10 to 30, preferably about 15–20 hours.

In order to bind the hydrochloric acid that is released, the reaction is preferably carried out with addition of from 3 to 4 mol of base, preferably of a tertiary amine, for example triethylamine.

Instead of 2-trichloromethylbenzimidazole it is also possible to use benzimidazole-2-carboxylic acid halides, esters, amides or nitriles or the free acid.

Route C:

of the product can be carried out by column chromatography or by recrystallisation.

Using the same procedure compounds I according to the invention can be prepared from N-substituted o-phenylenediamines IV and 2-methylbenzazoles by heating with sulphur.

The N-substituted benzimidazol-2-yl-benzothiazoles can also be prepared by reacting compounds VII with 1.0 to 1.5 mol of aniline and 2.5 to 5 mol, preferably 3 mol, of sulphur. For this purpose the starting components are heated for 8 to 20 hours to 120 to 250° C., and preferably at about 200° C.

The reaction can be carried out in the absence of a solvent or in the presence of an inert, high-boiling solvent.

A further subject of the invention, therefore, are processes for preparing the compounds I

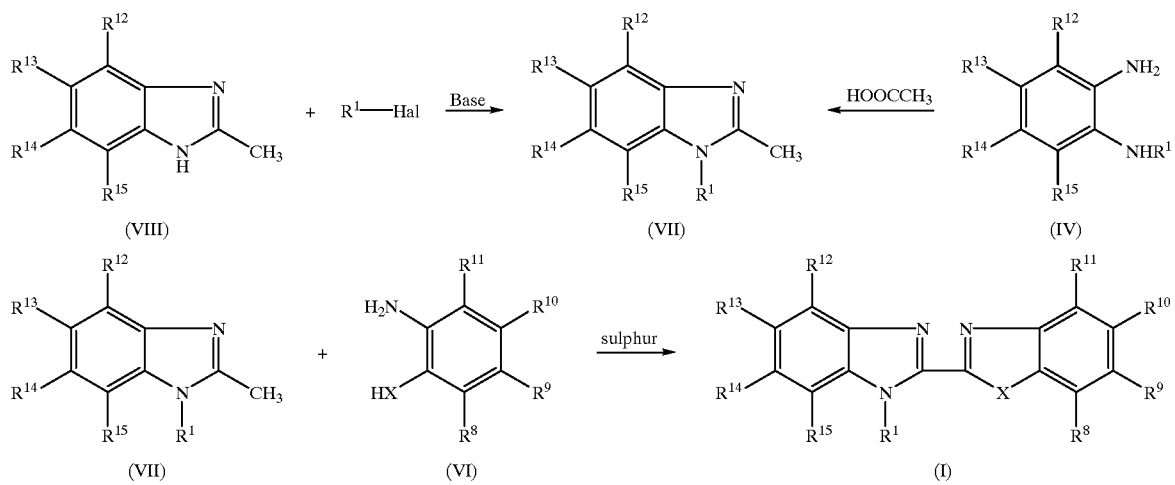

The corresponding N-substituted 2-methylbenzimidazoles VII can be prepared under alkaline conditions from 2-methylbenzimidazole VIII and organyl halides, suitable bases which can be used being alkali metal or alkaline earth metal hydrides, alcoholates, hydroxides or carbonates. In a preferred method of preparation the organylation is carried out in a 2-phase system consisting for example of a sodium hydroxide solution and a non-water-miscible organic solvent such as cyclohexane, toluene or xylene. The reaction can be carried out using a phase transfer catalyst, such as for example quaternary ammonium compounds, at temperatures of 20–90° C. The compounds VII can also be prepared from the N-substituted o-phenylenediamines, as described by M. A. Philips, J. Chem. Soc. 1928, 2393, by heating for 5 to 12 hours with acetic acid or acetic acid derivatives in 4N hydrochloric acid.

The N-substituted 2-methylbenzimidazoles VII can be converted into the compounds of the formula I by heating with equimolar quantities of o-phenylenediamine, o-aminophenol or o-aminothiophenol with the addition of 2.5 to 5 mol, preferably 3 mol, of sulphur. In a preferred variant the reaction is carried out by heating in pyridine for 8 to 30 hours. It can however also be carried out by heating the starting components to 180–250° C. for 8–15 hours both in the absence of a solvent and using an inert, high-boiling solvent such as for example N-methylpyrrolidone, 1,2,3,4-tetrahydronaphthalene or diethylene glycol monoethyl ether. After the reaction is complete the solvent is distilled off or the product is precipitated by adding water. The purification a) by reacting compounds II with $R^1$ halides,
b) by reacting 2-trichloromethylbenzimidazoles V with o-phenylenediamine, o-aminophenol or aminothiophenol, and
c) by reacting 2-methylbenzimidazole with o-phenylenediamine, o-aminophenol or o-aminothiophenol in the presence of sulfur.

Compounds of the formula I are known in principle from EP-A 669 223; however, compounds which are simultaneously substituted on the nitrogen and are free from sulfonic acid groups are not named therein. The compounds known from EP-A 669 323, therefore, are not a subject of the present invention. DE-A 27 33 439 discloses N-substituted benzimidazoles and their use as optical brighteners. Any indication toward the use of these compounds as UV absorbers is not contained in DE-A 27 33 439.

The compounds I can be used in particular in cosmetic pharmaceutical sunscreen compositions, products for hair care and day care with UV protection, but also as anti-ageing agents for industrial products.

They are notable for strong absorption both in the UV-B- and in the UV-A-I and -II regions. Furthermore, they have excellent photostability and good solubility in cosmetic solvents and in liquid, oil-soluble UV absorbers.

Because of their hydrophobic character, the UV absorbers I are also particularly suitable for the formulation of water-resistant sun protection products.

As UV-A/B broadband absorbers, when used in cosmetic or pharmaceutical preparations the absorbers I prevent the passage of UV rays through the applied film of the preparation. This is in general the case if the preparations contain from 0.5 to 15, preferably from 1 to 10, in particular from 2 to 7,% by weight (based on the overall weight of the preparation) of compound I.

The compounds I are also suitable for photostabilizing UV absorbers of low UV photostability. They are particularly successful in photostabilizing the very photounstable dibenzoylmethane compounds, especially 4-tert-butyl-4'-methoxydibenzoylmethane and 4-isopropyldibenzoylmethane.

The preparations comprising compounds I can be used for the protection of the skin and the hair—especially hair already damaged by permanent waving, dyeing and bleaching—against UV irradiation. These cosmetic and pharmaceutical preparations which are used to protect skin and hair against UV radiation can be present in the customarily used application forms, i.e. as an oil-in-water or water-in-oil emulsion, as a milk, as a lotion or cream, aerosol, hydrodispersion gel (emulsifier-free) or as any other customary cosmetic or pharmaceutical preparation. For the protection of the hair against UV rays, it is preferred to use preparations as a shampoo, conditioner, combination (i.e. 2 in 1), rinse, treatment, gel, lotion, spray or cream.

The cosmetic and pharmaceutical preparations can include the constituents customarily used in these compositions, such as emulsifiers, surface-active compounds, lanolin, vaseline, water, triglycerides of fatty acids, polyethylene glycols, fatty alcohols, ethoxylated fatty alcohols, fatty acid esters (for example isopropyl palmitate, isooctyl stearate, diisopropyl adipate, etc.), natural or synthetic oils or waxes, pigments (for example titanium dioxide, zinc oxide, pearl luster pigments, color pigments), thickeners (for example hydroxyethylcellulose, bentonite, etc.), preservatives, humectants, vitamins, silicone oils, glycerol, ethyl alcohol, perfume oils, chelating agents and antioxidants.

The compounds I can be employed individually or in a mixture in the corresponding preparations; they can also be employed in combination with UV absorbers of other classes of substance. Examples of such compounds include p-aminobenzoic acid
p-aminobenzoic acid ethyl ester (25 mol) ethoxylated
2-ethylhexyl p-dimethylaminobenzoate
p-aminobenzoic acid ethyl ester (2 mol) N-propoxylated
glycerol p-aminobenzoate
homomenthyl salicicylate
2-ethylhexyl salicylate
triethanolamine salicylate
4-isopropylbenzyl salicylate
menthyl anthranilate
ethyl diisopropylcinnamate
2-ethylhexyl p-methoxycinnamate
methyl diisopropylcinnamate
isoamyl p-methoxycinnamate
p-methoxycinnamic acid diethanolamine salt
isopropyl p-methoxycinnamate
2-ethylhexyl 2-cyano-3,3-diphenylacrylate
ethyl 2-cyano-3,3'-diphenylacrylate
2-phenylbenzimidazolesulfonic acid and its salts
3-(4'-trimethylammonium)-benzylidene-bornan-2-one methyl sulfate
terephthalylidene-dibornanesulfonic acid and its salts
4-tert-butyl-4'-methoxy-dibenzoylmethane
β-imidazole-4(5)-acrylic acid (urocaninic acid)
2-hydroxy-4-methoxybenzophenone
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methylbenzophenone
3-(4'-sulfo)benzylidene-bornan-2-one and its salts
3-(4'-methylbenzylidene)-d-1-camphor
4-isopropyldibenzoylmethane
2,4,6-trianilino-(p-carbo-2'-ethylhexyl-1'-oxy)-1,3,5-triazine
phenylene-bis-benzimidazyl-tetrasulfonic acid and its salts
N-(2 and 4)-[2-oxoborn-3-ylidene)methyl]benzyl] acrylamide polymer
polysiloxane malonates.

Particularly suitable UV absorbers are:
2-ethylhexyl p-methoxycinnamate,
isoamyl p-methoxycinnamate,
2-phenylbenzimidazolesulfonic acid,
3-(4'-methylbenzylidene)-d-1-camphor,
2-ethylhexyl 2-cyano-3,3-diphenylacrylate,
2-ethylhexyl salicylate,
4-tert-butyl-4'-methoxydibenzoylmethane,
phenylene-bis-benzimidazyl-tetrasulfonic acid and its salts,,
menthylanthranilate and
2,4,6-trianilino-(p-carbo-2'-ethylhexyl-1'-oxy)-1,3,5-triazine.

It is likewise possible to combine the compounds I with finely divided pigments (coated or uncoated), for example titanium dioxide, zinc oxide and iron oxide, in sun protection products and day care products with UV protection.

In addition, the compounds I according to the invention can also be combined with UV absorbers which are employed for industrial product protection. Examples of such UV absorbers correspond predominantly to compounds from the series of the benzotriazoles, benzophenones and malonates.

The percentages in the examples below relate in each case to the weight. Unless specified otherwise, the compounds were separated or purified by column chromatography on silica sol 60 (elution with n-hexane/ethyl acetate=(5–10):1).

EXAMPLES

Examples 1–13

General Procedure for Preparing benzimidazol-2-yl-benzoxazoles (Route A)

7.05 g (0.03 mol) of 2-(benzimidazol-2-yl)-benzoxazole are charged to 50 ml of dimethylformamide, 0.72 g (0.03 mol) of sodium hydride or 4.8 g (0.03 mol) of 50% strength sodium hydroxide solution are added, and the mixture is heated at 90° C. for 60 minutes. Then 0.045 mol of the corresponding alkyl bromide or chloride, for the compounds in Examples 10 and 11 4.32 g (0.06 mol) of 1,2-epoxybutane, is added and the mixture is stirred at 120° C. for 8 hours. After cooling to room temperature, the crude product is precipitated by addition of water and purified by recrystallization or column chromatography.

Example 14

2-(1-(2-Ethylhexyl)benzimidazol-2-yl)-benzoxazole (Route C)

24.4 g (0.1 mol) of 1-(2-ethylhexyl)-2-methylbenzimidazole (prepared by heating N-2-ethylhexyl-o-phenylenediamine in acetic acid/hydrochloric acid), 10.9 g (0.1 mol) of o-aminophenol and 9.6 g (0.3 mol) of sulfur in 100 ml of pyridine are heated under reflux for 18 hours. After cooling to room temperature, the crude product is precipitated by addition of water. Multiple recrystallization from n-hexane with addition of active charcoal gives 5.7 g (16% of theory) of product, which according to melting point, HPLC and UV determination is identical to the compound obtained in Example 7.

Example 15

2-(1-(2-Ethylhexyl)-benzimidazol-2-yl)-benzoxazole (Route B)

28.2 g (0.12 mol) of 1-(2-ethylhexyl)-2-trichloromethylbenzimidazole (prepared by reacting N-2-ethylhexyl-o-phenylenediamine with trichloroacetamido methyl ester), 13.1 g (0.12 mol) of o-aminophenol and 39.4 g (0.38 mol) of triethylamine in 150 ml of ethanol are stirred at room temperature for 15 hours. The ethanol is subsequently removed on a rotary evaporator, ethyl acetate is added to the residue which remains, and the mixture is washed with water and dried over sodium sulfate. 35% of product is identified by HPLC in the product mixture thus obtained; isolation can be carried out, for example, by column chromatography.

Examples 16–18

General Procedure for Preparing benzimidazol-2-yl-benzothiazoles 7.53 g (0.03 mol) of 2-(benzimidazol-2-yl)-benzothiazole are charged to 50 ml of dimethylformamide, 0.72 g (0.03 mol) of sodium hydride or 4.8 g (0.03 mol) of 50% strength sodium hydroxide solution are added, and the mixture is heated at 90° C. for 60 minutes. Then 0.045 mol of a corresponding alkyl bromide or alkyl chloride is added and the mixture is stirred at 120° C. for 8 hours. After cooling to room temperature, the crude product is precipitated by addition of water and purified by recrystallization or column chromatography.

Example 19

2-(1-(2-ethylhexyl)benzimidazol-2-yl)-benzothiazole (Route C)

48.8 g (0.2 mol) of 1-(2-ethylhexyl)-2-methylbenzimidazole (prepared by the alkylation of 2-methylbenzimidazole and 2-ethylhexyl bromide under phase transfer conditions), 25 g (0.2 mol) of o-aminothiophenol and 19.2 g (0.6 mol) of sulphur in 200 ml of pyridine are heated for 18 hours under reflux. Then the pyridine is distilled off and the remaining residue is dissolved by heating in 80 g of ethanol. After cooling, 55.2 g (76% of theory) of the product, which, according to its melting point and HPLC and UV analysis, is identical to the compound obtained in Example 18 by route A, are precipitated.

Example 20

2-(1-(2-ethylhexyl)benzimidazol-2-yl)-benzothiazole (Route C)

24.4 g (0.1 mol) of 1-(2-ethylhexyl)-2-methylbenzimidazole, 9.3 g (0.1 mol) of aniline and 9.6 g (0.3 mol) of sulphur are heated to 200° C. for 18 hours. After cooling to 60° C., 10 ml of ethanol are added and the insoluble components are filtered off. 54.4% of the product are identified in the resulting crude product by means of gas chromatography; isolation can for example be carried out by column chromatography.

Examples 21–27

General Procedure for Preparing 2,2'-bisbenzimidazoles 7.02 g (0.03 mol) of 2,2'-bisbenzimidazole are charged to 50 ml of dimethylformamide, 1.44 g (0.06 mol) of sodium hydride or 9.6 g (0.06 mol) of 50% strength sodium hydroxide solution are added, and the mixture is heated at 90° C. for 60 minutes. Then 0.09 mol of the corresponding alkyl bromide or alkyl chloride is added and the mixture is stirred at 120° C. for 8 hours. After cooling to room temperature, the crude product is precipitated by addition of water and purified by recrystallization or column chromatography.

Examples 28 and 29

1,1'-Dipentyl-5-methoxy- and 1,1'-dipentyl-6-methoxy-2,2'-bisbenzimidazole 7.9 g (0.03 mol) of 5-methoxy-2,2'-bisbenzimidazole are charged to 50 ml of dimethylformamide, 1.73 g (0.072 mol) of sodium hydride are added, and the mixture is heated at 90° C. for 60 minutes. Then 18.1 g (0.12 mol) of n-pentyl bromide are added and the mixture is stirred at 120° C. for 8 hours. After cooling to room temperature, the crude product is precipitated by addition of water. This product consists of a mixture of the isomeric 1,1'-dipentyl-5-methoxy- (26) and 1,1'-dipentyl-6-methoxy-2,2'-bisbenzimidazoles (27), which are separated by column chromatography on Chiracel OG (methanol/water=9:1).

Example 30

1,1'-Dipropyl-5,5'-dimethyl- and 1,1'-dipropyl-6,6'-dimethyl-2,2'-bisbenzimidazole 4.1 g (0.053 mol) of 5,5'-dimethyl-2,2'-bisbenzimidazole, 5.1 g (0.127 mol) of sodium hydride and 36 g (0.21 mol) of n-propyl iodide are reacted in analogy to the general procedure for the preparation of 2,2'-bisbenzimidazoles. The crude product obtained consists of a mixture of 1,1'-dipropyl-5,5'-dimethyl- and 1,1'-dipropyl-6,6'-dimethyl-2,2'-bisbenzimidazole, which is purified by column chromatography.

Benzimidazol-2-yl-benzoxazoles (1–13)

| Example | Compound | m.p. °C. | $\lambda_{max}$ | $E^{1/1}$ |
|---|---|---|---|---|
| 1 | [benzimidazole-benzoxazole with N-propyl] | 122 | 344<br>327 | 1000<br>1376 |
| 2 | [benzimidazole-benzoxazole with N-allyl] | 134 | 344<br>327 | 971<br>1351 |
| 3 | [benzimidazole-benzoxazole with N-pentyl] | 130 | 345<br>328 | 886<br>1236 |
| 4 | [benzimidazole-benzoxazole with N-isopentyl] | 141 | 345<br>327 | 906<br>1249 |
| 5 | [benzimidazole-benzoxazole with N-(CH$_2$)$_7$CH$_3$] | 132 | 345<br>328 | 774<br>1101 |
| 6 | [benzimidazole-benzoxazole with N-(CH$_2$)$_8$CH$_3$] | 113 | 345<br>327 | 756<br>1071 |

-continued

| Example | Compound | m.p. °C. | $\lambda_{max}$ | $E^{1/1}$ |
|---|---|---|---|---|
| 7 | | 109 | 345<br>327 | 737<br>1041 |
| 8 | | | 345<br>327 | 649<br>911 |
| 9 | | 185–187 | 344<br>327 | 792<br>1135 |
| 10 | | 221 | 318 | 654 |
| 11 | | 88–89 | 14 | 536 |
| 12 | | 204 | 343<br>326 | 884<br>1202 |

-continued

| Example | Compound | m.p. °C. | λ_max | E^{1/1} |
|---------|----------|----------|-------|---------|
| 13 | (2-ethylhexyl ester of benzimidazol-2-yl-benzoxazole N-acetic acid) | 132–134 | 344<br>327 | 637<br>869 |

Benzimidazol-2-yl-benzothiazoles (16–18)

| Example | Compound | m.p. °C. | λ^{max} | E^{1/1} |
|---------|----------|----------|---------|---------|
| 16 | (N-allyl benzimidazol-2-yl-benzothiazole) | 124 | 358<br>340 | 758<br>1103 |
| 17 | (N-isopentyl benzimidazol-2-yl-benzothiazole) | 110 | 358<br>341 | 710<br>1003 |
| 18 | (N-(2-ethylhexyl) benzimidazol-2-yl-benzothiazole) | 70 | 359<br>341 | 600<br>869 |

Bisbenzimidazoles (21–30)

| Example | Compound | m.p. °C. | $\lambda_{max}$ | $E^{1/1}$ |
|---|---|---|---|---|
| 21 | | 138 | 343<br>326<br>316 | 879<br>1242<br>1000 |
| 22 | | 105 | 313 | 738 |
| 23 | | 160 | 343<br>326 | 725<br>1036 |
| 24 | | 90 | 314 | 717 |
| 25 | | 70–71 | 314 | 692 |
| 26 | | 108 | 343<br>326 | 626<br>940 |

-continued

| | | | | |
|---|---|---|---|---|
| 27 | 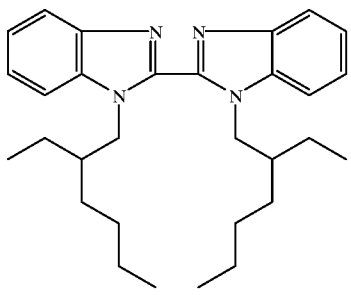 | 63 | 314 | 499 |
| 28 | 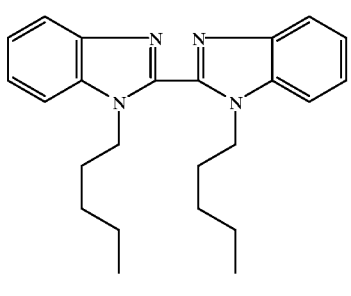 | | 328 | 543 |
| 29 | 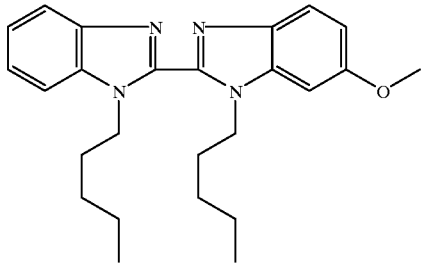 | | 324 | 346 |
| 30 | 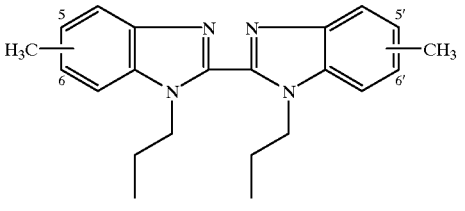 | | 319 | 738 |

| TRADE NAME | CHEMICAL DESIGNATION | SUPPLIER |
|---|---|---|
| Abil 100 | Polydimethylsiloxane | 7 |
| Antaron V-216 | Vinylpyrrolidone/hexadecene copolymer | 18 |
| Arlacel 1689 | Sorbitan monooleate/propylglyceryl 3-ricinoleate | 4 |
| Arlacel 165 | Glycerol stearate/polyethylene glycol (MW 100) stearate mixture | 4 |
| Arlatone G | Castor oil hydrogenated with 25 mol of ethylene oxide | 4 |
| Arlatone 983 S | Polyethylene glycol (MW 5) glyceryl stearate | 4 |
| Baysilone Fluid PK 20 | Silicone oil | 5 |
| Betone Gel MIO | Mineral oil, quaternium 18 hectorite, propylene carbonate | 17 |
| Brij 76 | Polyethylene glycol (MW 10) stearyl ester | 4 |
| Carbopol 2984 | Polyacrylic acid | 2 |
| Cetiol OE | Dicapryl ether | 3 |

-continued

| TRADE NAME | CHEMICAL DESIGNATION | SUPPLIER |
| --- | --- | --- |
| Cetiol SN | Cetyl/stearyl isononanoate | 3 |
| Copherol F 1250 | D-α-tocopheryl acetate | 3 |
| Cutina CBS | Glycerol stearate, cetyl/stearyl alcohol, cetyl palmitate, coconut glycerides | 3 |
| Cutina FS 45 | Fatty acid mixture of palmitic and stearic acid | 3 |
| Cutina MD | Glyceryl stearate | 3 |
| Dehymuls PG PH | Polyglycerol poly-12-hydroxystearate | 3 |
| Diisopropyl adipate | Adipic acid diisopropyl ester | 15 |
| D-Panthenol | Pantothenyl alcohol | 6 |
| Eusolex TA | Titanium dioxide | 13 |
| Eutanol G | 2-Octyldodecanol | 3 |
| Eumulgin B1 | Cetyl/stearyl alcohol, etherified with 12 mol of ethylene oxide | 3 |
| Eumulgin B2 | Cetyl/stearyl alcohol, etherified with 20 mol of ethylene oxide | 3 |
| Finsolv TN | Alkyl benzoate | 12 |
| Genapol LRO liq. | Sodium lauryl sulfate | 9 |
| Glycerol | 1,2,3-Propanetriol | 3 |
| Isopropylmyristate | Myristic acid isopropyl ester | 3 |
| Jojoba oil | Jojoba oil | 19 |
| Lampeon S | Protein/coconut fatty acid condensate, potassium salt | 3 |
| Lanette O | Cetyl/stearyl alcohol mixture | 3 |
| Macadamia nut oil | Macadamia nut oil | 20 |
| Myritol 318 | Caprylic/capric triglyceride | 3 |
| Natrosol 250 HHR | Hydroxyethylcellulose | 11 |
| NEO HELIOPAN ® AV | Isooctyl p-methoxycinnamate | 1 |
| NEO HELIOPAN ® E 1000 | Isoamyl p-methoxycinnamate | 1 |
| NEO HELIOPAN ® HYDRO | Phenylbenzimidazolesulfonic acid | 1 |
| NEO HELIOPAN ® MBC | 3-(4-methylbenzylidene)-d,1-camphor | 1 |
| NEO HELIOPAN ® OS | 2-Ethylhexyl salicylate | 1 |
| Olive oil | Olive oil | 21 |
| Permulgin 2550 | Wax | 14 |
| Permulgin 3220 | Wax | 14 |
| Phenonip | Mixture of p-hydroxybenzoic esters and phenoxyethanol | 8 |
| Polymer JR 400 | Polyquaternium-10 | 21 |
| 1,2-Propylene glycol | 1,2-Propanediole | 6 |
| Texapon MG 3 | Magnesium lauryl sulfate/disodium lauryl sulfosuccinate | 3 |
| Tocopherole oil | Soya oil with D-α-tocopherole | 22 |
| Uvinul T 150 | Isooctyl triazinyl-p-aminobenzoate | 6 |
| Veegum Ultra | Magnesium aluminum silicate | 10 |
| ZINC OXIDE NEUTRAL H&R | Zinc oxide | 1 |
| Zinc stearate | Zinc stearate | 16 |

SUPPLIERS
 1. Haarmann & Reimer GmbH, Holzminden
 2. B. F. Goodrich Company, Neuss
 3. Henkel KGaA, Düsseldorf
 4. ICI Speciality Chemicals, Frankfurt
 5. Bayer AG, Leverkusen
 6. BASF, Ludwigshafen
 7. Goldschmidt AG, Essen
 8. Nipa Lab. Ltd. Pontypridd, Mid. Glam., Wales/GB
 9. Hoechst AG, Frankfurt
10. R. T. Vanderbilt Company Inc., Norwalk/USA
11. Hercules Inc., Wilmington, Delaware/USA
12. Witco Surfactants GmbH, Steinau a.d. Straβe
13. E. Merck, Darmstadt
14. Koster Keunen Holland BV, Bladl/NL
15. Akzo Chemie GmbH, Düren
16. Chemische Werke Barlocher, Munich
17. Rheox Inc., Hightstown, New Jersey/USA
18. ISP Global Technologies Deutschland GmbH, Frechen
19. Henry Lamotte, Bremen
20. Erhard Wagner GmbH, Bremen
21. Nordmann & Rassmann GmbH & Co., Hamburg
22. Richter GmbH, Berlin

Example 31

SUN PROTECTION LOTION (O/W)

| | CONSTITUENTS | % |
|---|---|---|
| A) | Arlatone 983 S | 1.75 |
| | Brij 76 | 1.25 |
| | Lanette O | 1.15 |
| | Myritol 318 | 5.00 |
| | Eutanol G | 30.00 |
| | Cetiol SN | 5.00 |
| | UV absorber of the formula (I) | 2.00 |
| B) | Water, distilled | 24.65 |
| | 1,2-Propylene glycol | 2.00 |
| | Phenonip | 0.50 |
| C) | Water, distilled | 25.00 |
| | Carbopol 2984 | 0.30 |
| | Sodium hydroxide, 10% strength in water | 1.00 |
| D) | Perfume oil | 0.40 |

PREPARATION INSTRUCTIONS:

Part A: Melt at about 80° C.
Part B: Heat to about 90° C. Add part B with stirring to part A.
Part C: Disperse Carbopol without lumps in water, neutralize with sodium hydroxide solution to form a gel, add at about 60° C. to part A/B. Cool with stirring to room temperature.
Part D: Perfume the emulsion at about 30° C. Monitor pH (6.5 to 7.0).

Example 32

SUN PROTECTION MILK (W/O)

| | CONSTITUENTS | % |
|---|---|---|
| A) | Dehymuls PG PH | 5.00 |
| | Permulgin 3220 | 0.50 |
| | Zinc stearate | 0.50 |
| | Finsolv TN | 19.00 |
| | Eutanol G | 19.00 |
| | UV Absorber of the formula (I) | 2.00 |
| B) | Water, distilled | 47.50 |
| | Glycerol 86% | 5.00 |
| | Magnesium sulfate 7 $H_2O$ | 0.50 |
| | Phenonip | 0.50 |
| C) | Perfume oil | 0.50 |

PREPARATION INSTRUCTIONS:

Part A: Melt at about 90° C.
Part B: Heat to about 95° C., then add part B with stirring to part A. Cool with stirring to room temperature.
Part C: Add part C at 30° C. and then homogenize.

Example 33

SUN PROTECTION MILK (W/O)

| | CONSTITUENTS | % |
|---|---|---|
| A) | Arlacel 165 | 3.00 |
| | Eumulgin B 2 | 1.00 |
| | Lanette O | 1.00 |
| | Myritol 318 | 3.00 |
| | Cetiol OE | 2.00 |
| | Abil 100 | 1.00 |
| | Bentone Gel M10 | 3.00 |
| | Cutina CBS | 1.00 |
| | Phenonip | 0.20 |
| | NEO HELIOPAN ® (octyl salicylate) | 3.00 |
| | NEO HELIOPAN ® AV (octyl methoxycinnamate) | 5.00 |
| | NEO HELIOPAN ® E 1000 (isoamyl p-methoxycinnamate) | 5.00 |
| | NEO HELIOPAN ® MBC (4-methylbenzylidene camphor) | 1.00 |
| | Eusolex TA | 3.00 |
| | UV Absorber of the formula (I) | 2.00 |
| | Eutanol G | 30.00 |
| B) | Water, distilled | 17.60 |
| | Glycerol 86% strength | 3.00 |
| | Phenonip | 0.30 |
| | Veegum Ultra | 1.00 |
| | Natrosol 250 HHR | 0.30 |
| | NEO HELIOPAN ® HYDRO, employed as a 15% strength solution after neutralization with sodium hydroxide (phenylbenzimidazolesulfonic acid) corresponds to active substance: 2.0% | 13.30 |
| C) | Perfume oil | 0.30 |

PREPARATION INSTRUCTIONS:

Part A: Melt at about 80° C., then carefully disperse Eusolex TA.
Part B: Heat to about 90° C. without Veegum and Natrosol, then disperse Veegum and Natrosol. Add part B with stirring to Part A. Cool with stirring to room temperature.
Part C: Add part C at 30° C. then homogenize. Check pH (7.0–7.5).

Example 34

SUN PROTECTION LOTION (W/O)

| | CONSTITUENTS | % |
|---|---|---|
| A) | Arlacel 1689 | 3.50 |
| | Finsolv TN | 6.00 |
| | NEO HELIOPAN ® E 1000 (isoamyl p-methoxycinnamate) | 7.00 |
| | Uvinul T 150 (octyl triazone) | 1.00 |
| | UV Absorber of the formula (I) | 2.00 |
| | Copherol F 1250 | 2.00 |
| | Permulgin 2550 | 1.00 |
| | Myritol 318 | 6.00 |
| | Eutanol G | 28.50 |
| | ZINC OXIDE NEUTRAL H&R (zinc oxide) | 7.00 |
| B) | Water, distilled | 30.20 |
| | Glycerol 86% | 5.00 |
| | Phenonip | 0.50 |
| C) | Perfume oil | 0.30 |

PREPARATION INSTRUCTIONS:

Part A: Carefully melt at about 90° C. (without ZINC OXIDE NEUTRAL H&R). Then carefully disperse ZINC OXIDE NEUTRAL H&R.
Part B: Heat to about 95° C., then add part B with stirring to part A. Cool with stirring to room temperature.
Part C: Add part C at 30° C. and then homogenize.

Example 35

SUN PROTECTION OIL

| | CONSTITUENTS | % |
|---|---|---|
| A) | NEO HELIOPAN ® E 1000 (isoamyl p-methoxycinnamate) | 7.50 |
| | NEO HELIOPAN ® OS (octyl salicylate) | 5.00 |
| | UV Absorber of the formula (I) | 3.00 |
| | Myritol 318 | 34.70 |
| | Diisopropyl adipate | 5.00 |

-continued

| | | |
|---|---|---|
| Olive oil | | 1.00 |
| Jojoba oil | | 1.00 |
| Macadamia nut oil | | 1.00 |
| Tocopherol oil | | 1.00 |
| Isopropyl myristate | | 35.00 |
| Antaron V-216 | | 5.00 |
| Phenonip | | 0.50 |
| Perfume oil | | 0.30 |

PREPARATION INSTRUCTIONS:

Carefully mix all of the constituents, then heat gently if necessary until all of the constituents are dissolved.

Example 36

| SUN PROTECTION LOTION (O/W) | | |
|---|---|---|
| | CONSTITUENTS | % |
| A) | Cutina FS 45 | 2.00 |
| | Eumulgin B1 | 0.25 |
| | Eumulgin B2 | 0.25 |
| | Cutina MD | 2.00 |
| | Lanette O | 2.80 |
| | Eutanol G | 19.00 |
| | Finsolv TN | 19.00 |
| | UV Absorber of the formula (I) | 2.00 |
| B) | Water, distilled | 24.90 |
| | Phenonip | 0.50 |
| C) | Water, distilled | 25.00 |
| | Carbopol 2984 | 0.40 |
| | Sodium hydroxide, 10% strength in water | 1.50 |
| D) | Perfume oil | 0.40 |

PREPARATION INSTRUCTIONS:

Part A: Melt at about 80° C.
Part B: Heat to about 90° C. Add part B with stirring to part A.
Part C: Disperse Carbopol without lumps in water, neutralize with sodium hydroxide solution to form a gel, add at about 60° C. to part A/B. Cool with stirring to room temperature.
Part D: Perfume the emulsion at about 30° C. Monitor pH (6.5 to 7.0).

Example 37

| HAIR SHAMPOO | | |
|---|---|---|
| | CONSTITUENTS | % |
| A) | Genapol LRO liquid | 18.00 |
| | Texapon MG3 | 36.00 |
| | Lamepon S | 6.00 |
| | Perfume oil | 0.60 |
| | Phenonip | 0.50 |
| | Arlatone G | 2.00 |
| | UV Absorber of the formula (I) | 0.20 |
| | NEO HELIOPAN ® E 1000 (isoamyl p-methoxycinnamate) | 1.00 |
| B) | Water, distilled | 33.30 |
| | Polymer JR 400 | 0.20 |
| | D-Panthenol | 1.00 |
| | Sodium chloride | 1.00 |

PREPARATION INSTRUCTIONS:

Part A: Dissolve UV absorber in NEO HELIOPAN ® E 1000 and Phenonip with gentle heating, then add Arlatone G and perfume oil and mix thoroughly. Weigh in the remaining constituents.
Part B: Dissolve polymer with stirring in water, add remaining constituents and dissolve. Add part B to part A with stirring (monitor pH, about 5.5).

We claim:

1. A compound of the formula

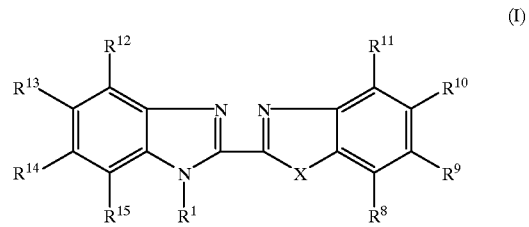

in which

X is S, NH, $NR^1$ or O, $R^1$ is $C_5$–$C_{20}$-alkyl, optionally substituted by $C_1$–$C_{12}$-alkoxy, $C_6$–$C_{12}$-aryloxy, amino, hydroxyl, $CONR^2R^3$, $COOR^4$ or $Si(OR^7)_3$, $R^2$ and $R^3$ independently of one another are H or $C_1$–$C_{16}$-alkyl, $R^4$ is H, $C_1$–$C_{16}$-alkyl, $C_6$–$C_{12}$-aryl or $R^5$—O—$(CH_2$—$CH(R^6)$—O—$)_n$—$CH_2$—$CH(R^6)$—, $R^5$ is $C_1$–$C_4$-alkyl, $R^6$ is H or methyl, n is zero or an integer from 1 to 4, $R^7$ is $C_1$–$C_4$-alkyl and $R^8$ to $R^{15}$ independently of one another are hydrogen, amino or nitro or posses the meaning given under $R^1$.

* * * * *